(12) United States Patent
Fujii et al.

(10) Patent No.: US 6,232,323 B1
(45) Date of Patent: May 15, 2001

(54) CRYSTALS OF PIPERIDINE DERIVATIVES, INTERMEDIATES FOR PRODUCTION OF THE SAME, AND PROCESS FOR PRODUCING THE SAME

(75) Inventors: Akiko Fujii; Mie Kubo; Tomoya Yamamoto; Jiro Shimada; Ryuichi Mihara; Hirokazu Naora; Koji Asai, all of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/672,080

(22) Filed: Sep. 29, 2000

Related U.S. Application Data

(63) Continuation of application No. 08/735,696, filed on Oct. 23, 1996.

(30) Foreign Application Priority Data

Oct. 23, 1995 (JP) .................................................. 7-274175
Oct. 3, 1996 (JP) .................................................. 8-263010

(51) Int. Cl.$^7$ ........................ A61K 31/445; C07D 401/12
(52) U.S. Cl. ............................................ 514/316; 546/191
(58) Field of Search .............................. 514/316; 546/191

(56) References Cited

U.S. PATENT DOCUMENTS 5,932,593 * 8/1999 Makino et al. ...................... 514/316

* cited by examiner

*Primary Examiner*—Ceila Chang
(74) *Attorney, Agent, or Firm*—Oblon, Spivak, McClelland, Maier & Neustadt, P.C.

(57) ABSTRACT

Monohydrate and trihydrate crystals of N-(2-(4-(5H-dibenzo[a,d]cyclohepten-5-ylidene)-piperidino) ethyl)-1-formyl-4-piperidinecarboxamide hydrochloride having excellent stability.

8 Claims, 9 Drawing Sheets

CRYSTALS OF PIPERIDINE DERIVATIVES, INTERMEDIATES FOR PRODUCTION OF THE SAME, AND PROCESS FOR PRODUCING THE SAME

This application is a continuation of application Ser. No. 08/735,696, filed Oct. 23, 1996.

BACKGROUND OF THE INVENTION

1. Field of the Invention

The present invention relates to crystals of N-(2(4-(5H-dibenzo[a,d]cyclohepten-5-ylidene)piperidino)ethyl)-1-formyl-4-piperidinecarboxamide hydrochloride, intermediates for production of the same, and a process for producing the same.

2. Description of the Background

N-(2-(4-(5H-dibenzo[a,d]cyclohepten-5-ylidene)-piperidino)ethyl)-1-formyl-4-piperidinecarboxamide hydrochloride, hereinafter referred to as Compound (I) at times has the formula (I):

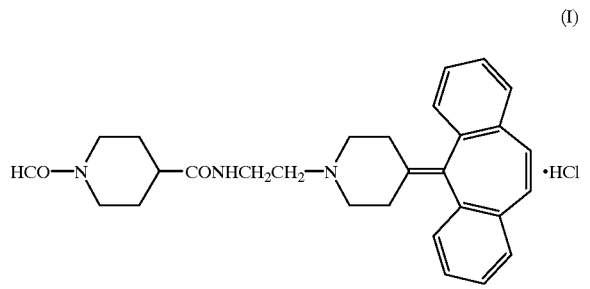

(I)

and exhibits anti-hypertensive activity as well as activity in controlling platelet agglutination. Thus, this compound is useful in pharmaceutical preparations. However, crystals thereof are as yet unknown.

SUMMARY OF THE INVENTION

Accordingly, it is an object of the present invention to provide crystals of N-(2-(4-(5H-dibenzo[a,d]cyclohepten-5-ylidene)-piperidino)ethyl)-1-formyl-4-piperidinecarboxamide hydrochloride.

It is also an object of the present invention to provide an intermediate compound for preparing the compound of the formula (I).

It is, moveover, an object of the present invention to provide a process for producing the compound of the formula The above objects and others are provided by crystals of N-(2-(4-(5H-dibenzo(a,d)cyclohepten-5-ylidene)-piperidino)ethyl)-1-formyl-4-piperidinecarboxamide hydrochloride monohydrate.

DETAILED DESCRIPTION OF THE PREFERRED EMBODIMENTS

In accordance with the present invention, crystals of N-(2-(4-(5H-dibenzo[a,d]cyclohepten-5-ylidene)-piperidino)ethyl)-1-formyl-4-piperidinecarboxamide hydrochloride are provided. More specifically, two types of crystals, each in the form of a hydrate, are provided. These crystals exhibit unexpected stability, while one of the crystals further exhibits excellent oral absorption and the other exhibits a high dissolution rate. These surprising discoveries have led to the present invention.

In more detail, the present invention relates to crystals of N-(2-(4-(5H-dibenzo[a,d]cyclohepten-5-ylidene)-piperidino)ethyl)-1-formyl-4-piperidinecarboxamide hydrochloride monohydrate, crystals of N-(2-(4-(5H-dibenzo[a,d]cyclohepten-5-ylidene)-piperidino)ethyl)-1-formyl-4-piperidinecarboxamide hydrochloride trihydrate, and intermediates for production of the same, as well as a process for producing the same.

Figure 1:
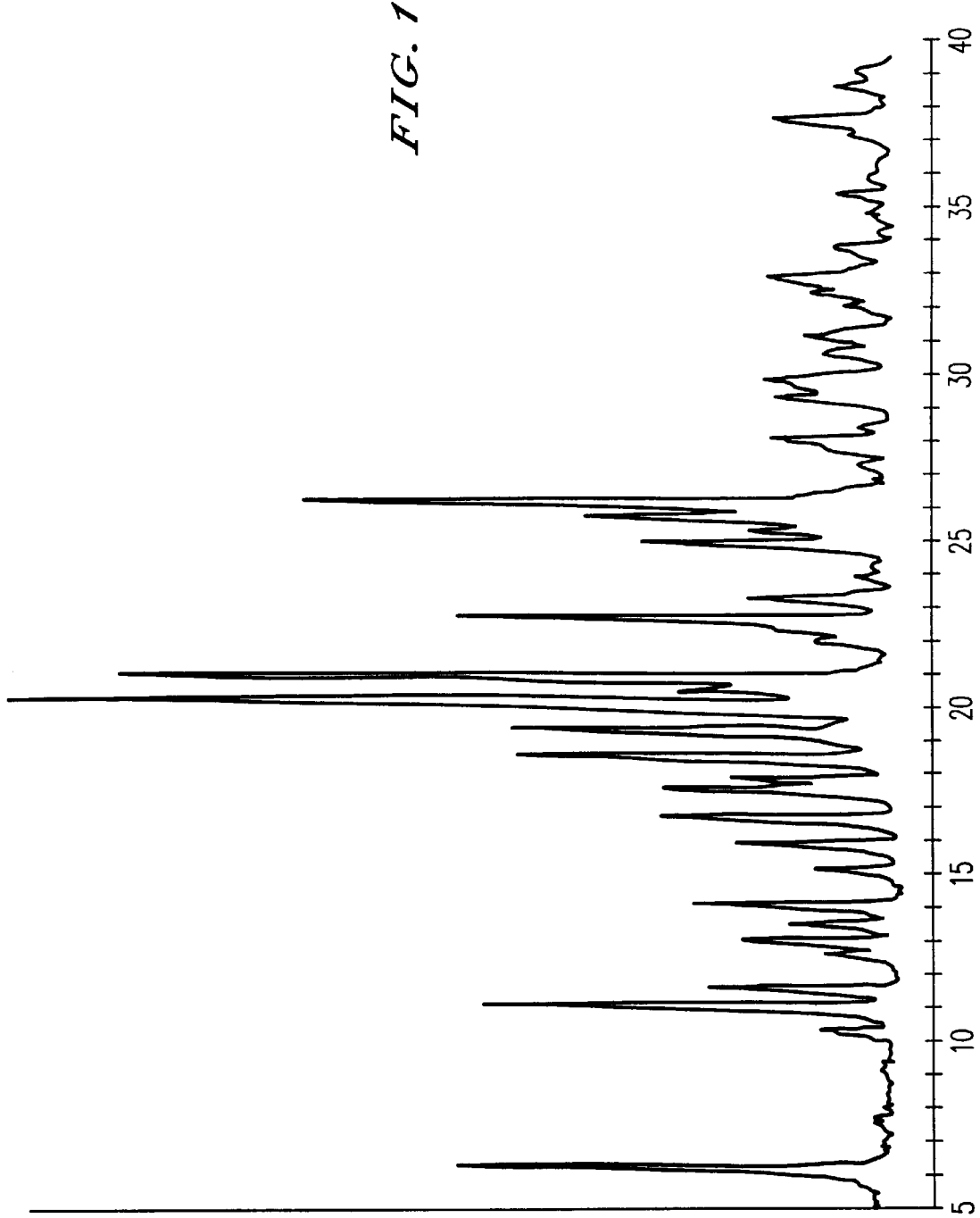
FIG. 1 is a powder X-ray diffraction pattern of monohydrate crystals.
Figure 2:
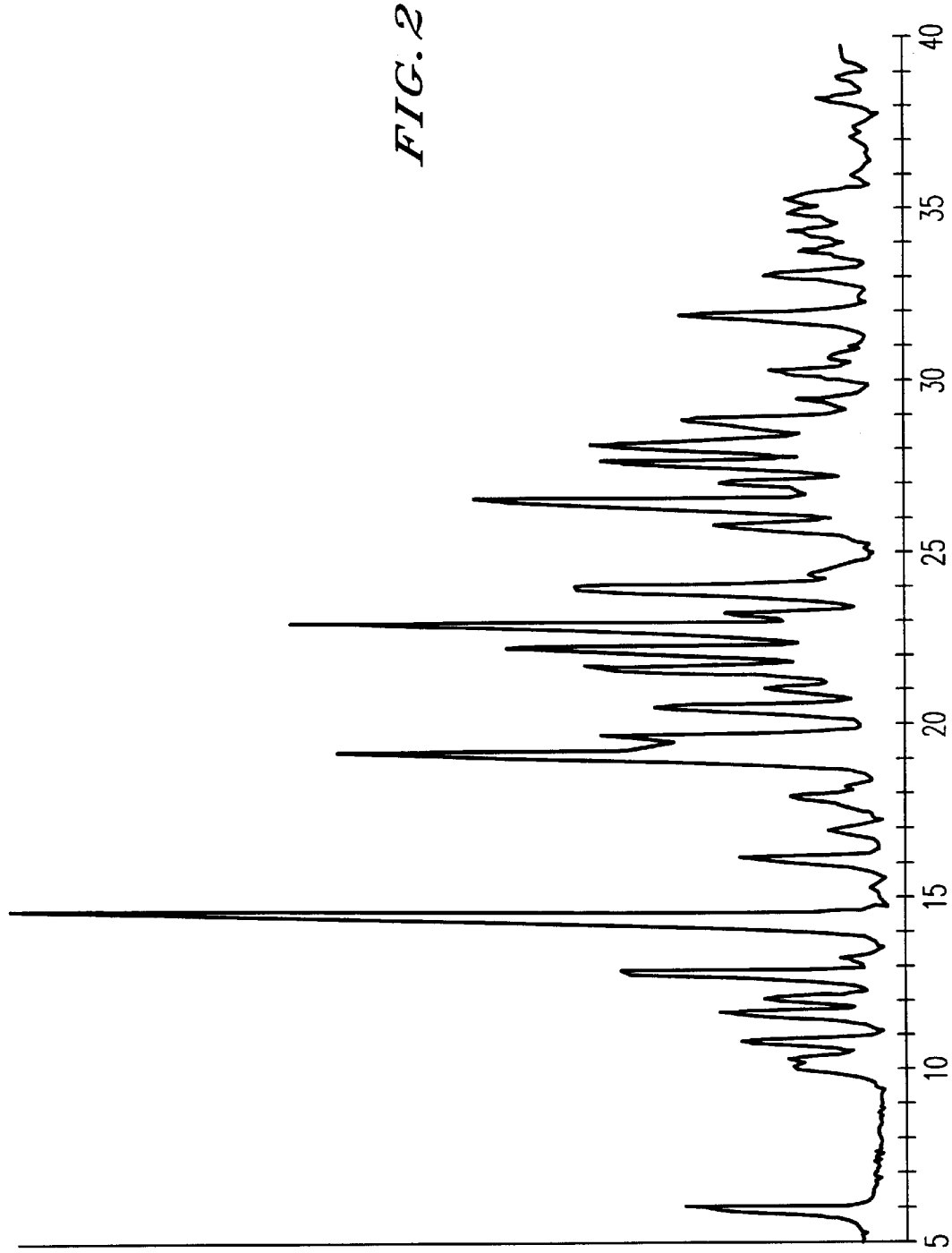
FIG. 2 is a powder X-ray diffraction pattern of trihydrate crystals.
Figure 3:
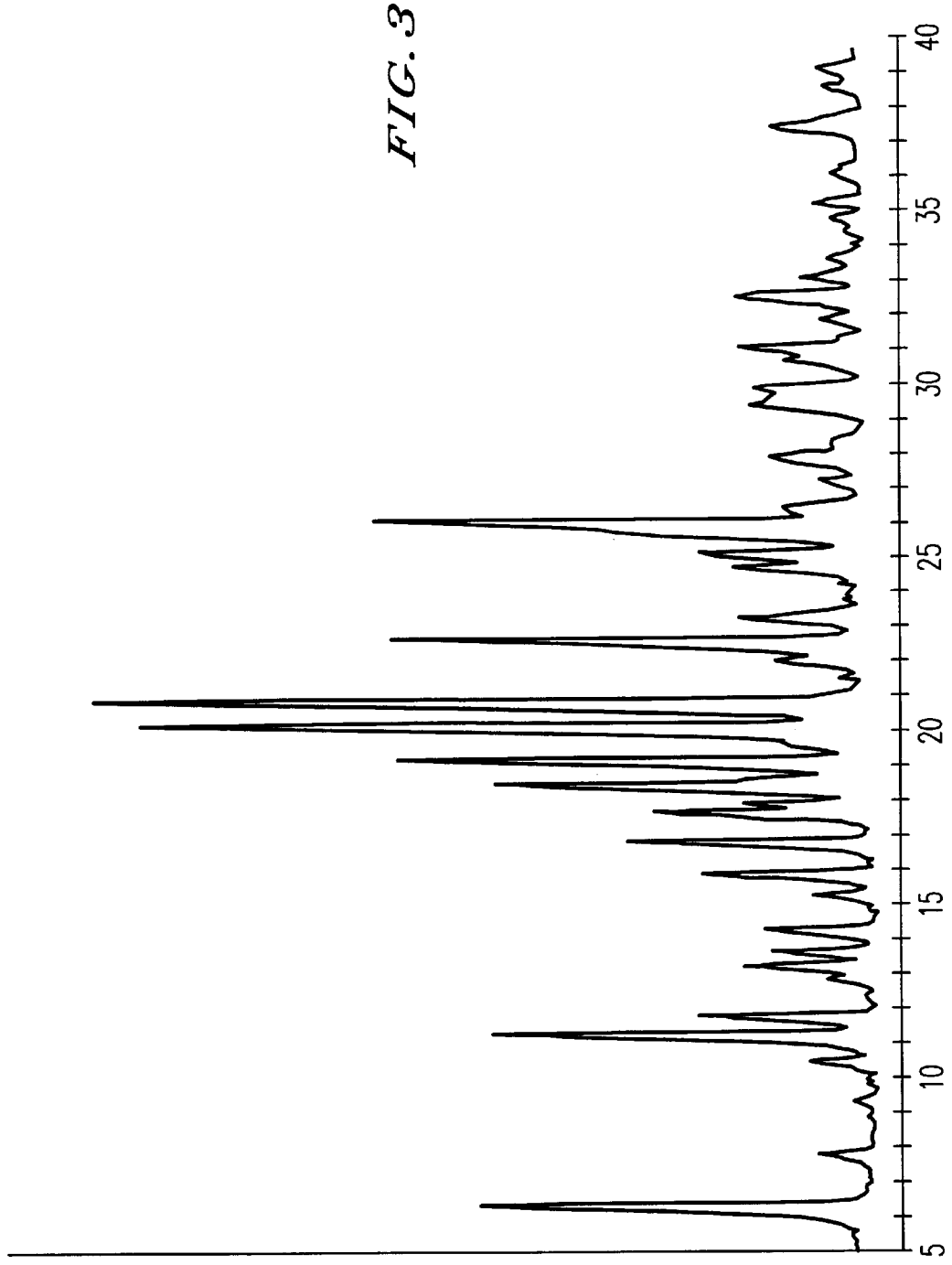
FIG. 3 is a powder X-ray diffraction pattern of α-type anhydride crystals.
Figure 4:
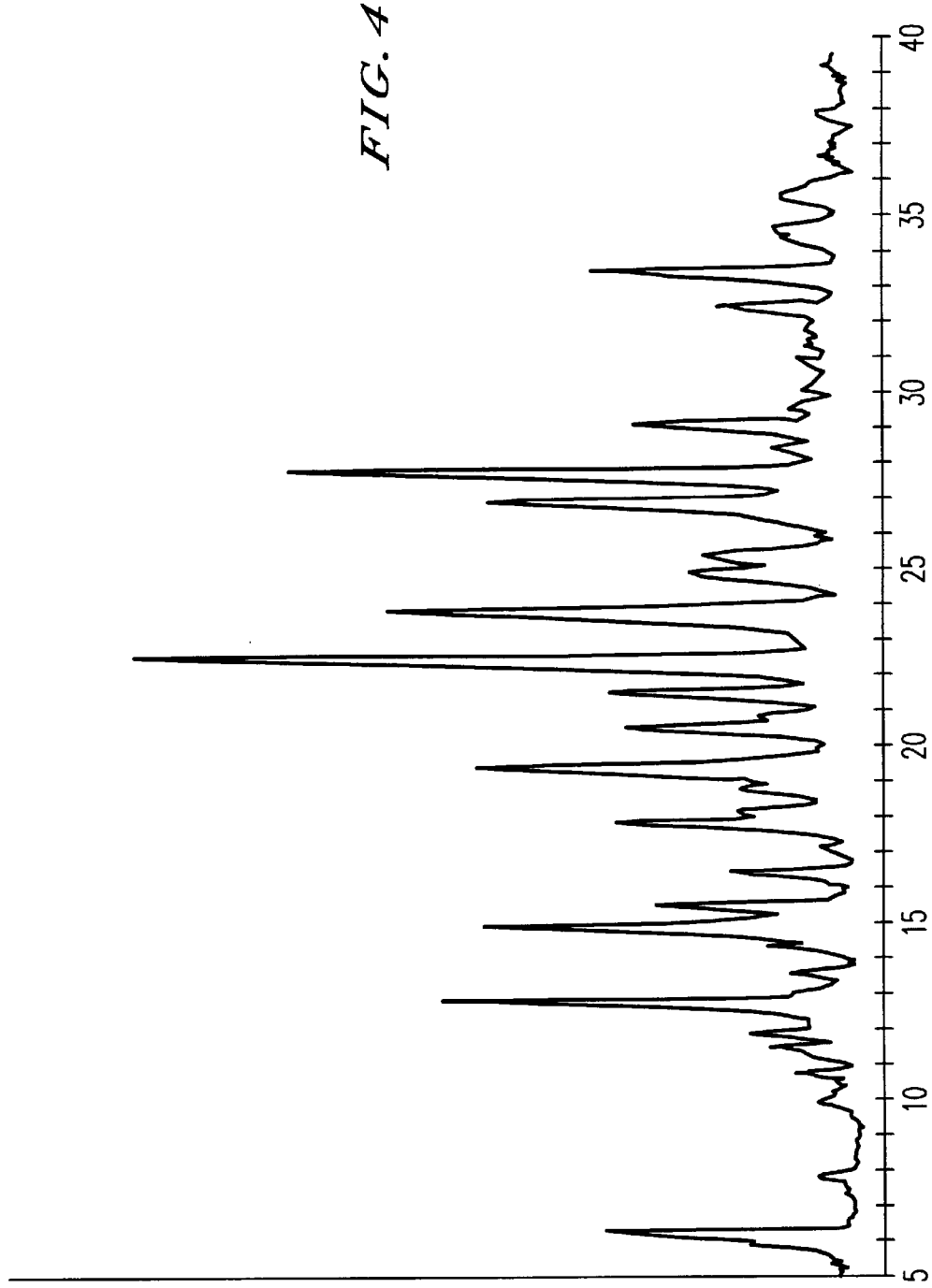
FIG. 4 is a powder X-ray diffraction pattern of β-type anhydride crystals.
Figure 5:
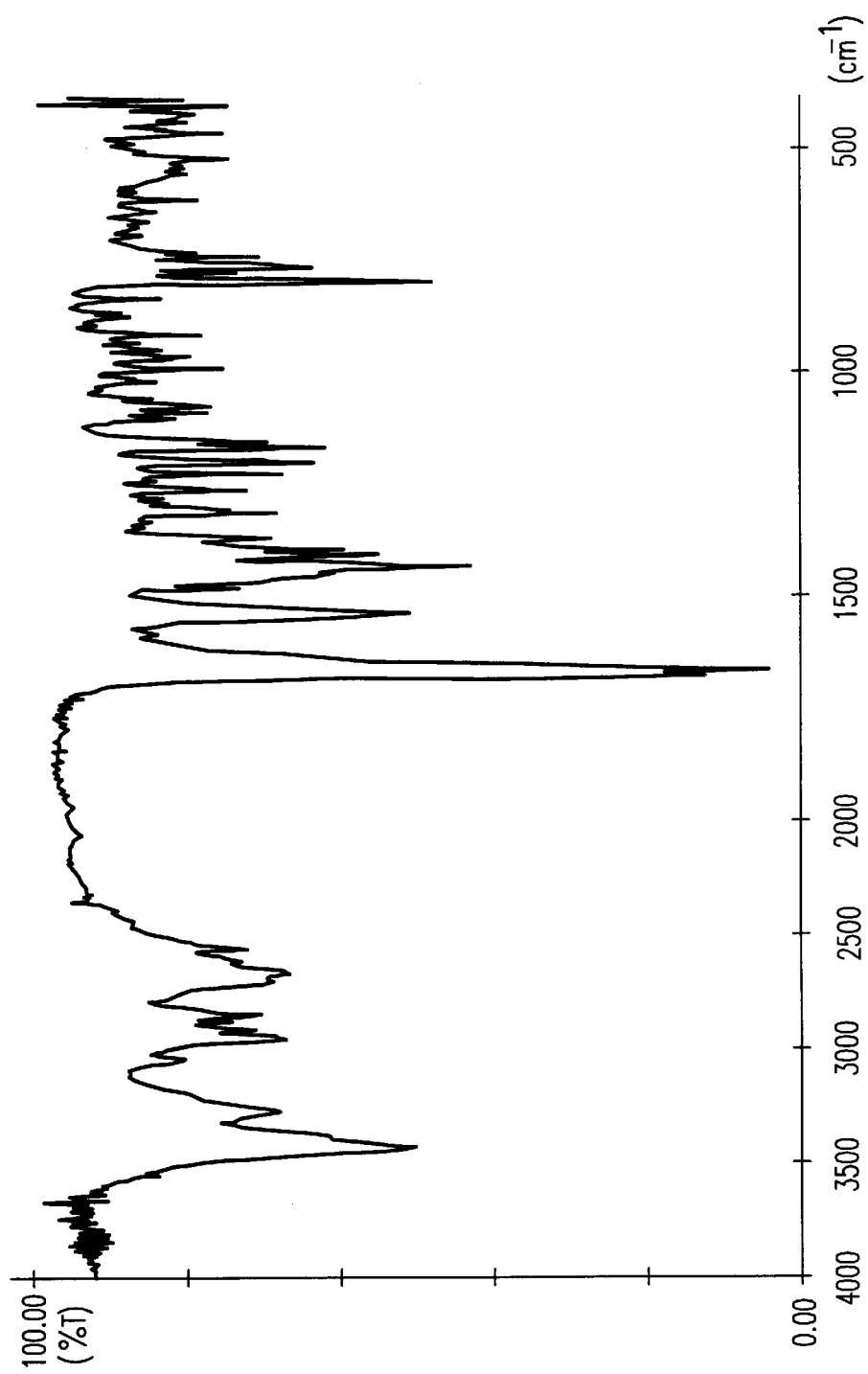
FIG. 5 is an infra-red (IR), absorption spectrum of monohydrate crystals.
Figure 6:
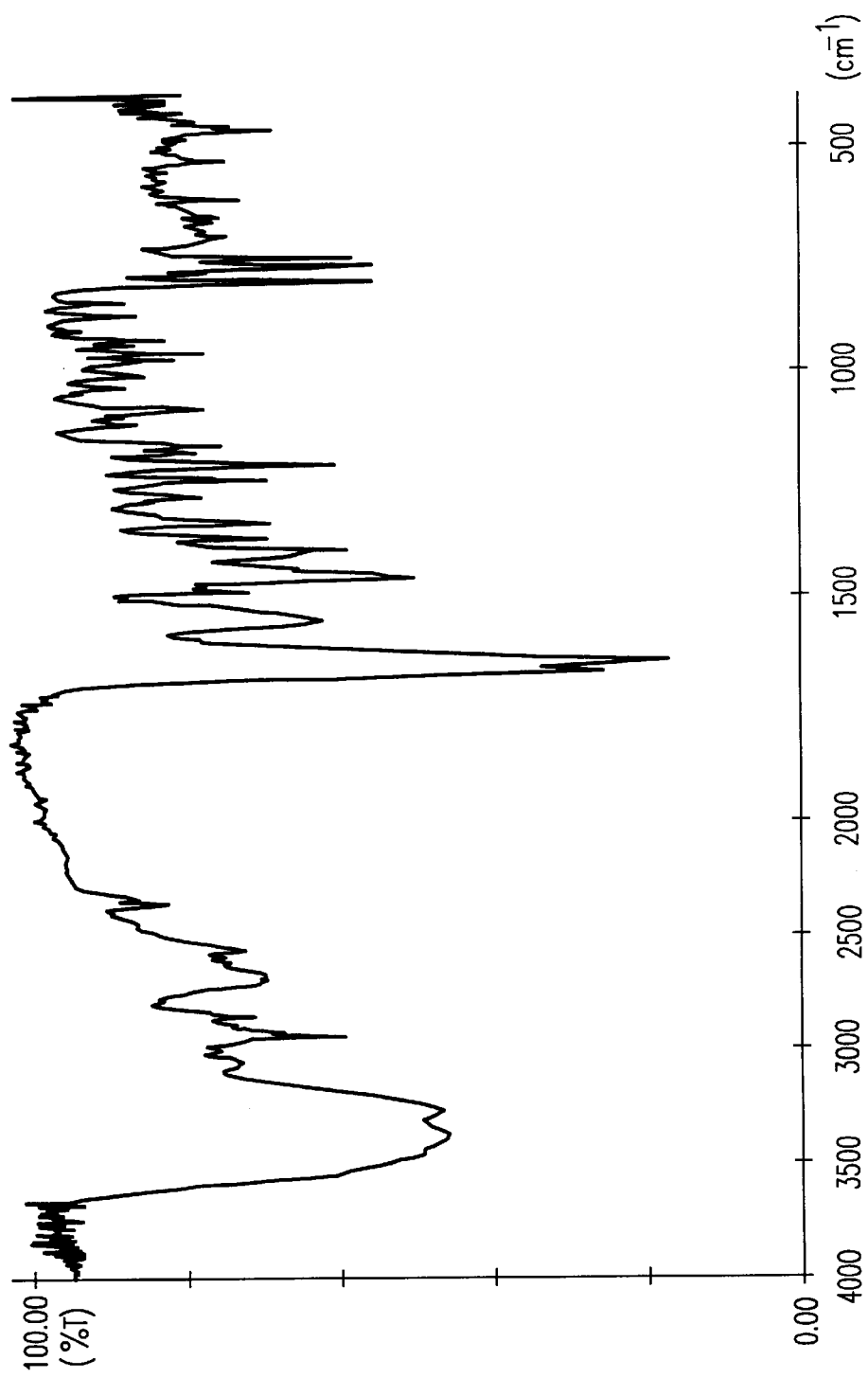
FIG. 6 is an IR absorption spectrum of trihydrate crystals.
Figure 7:
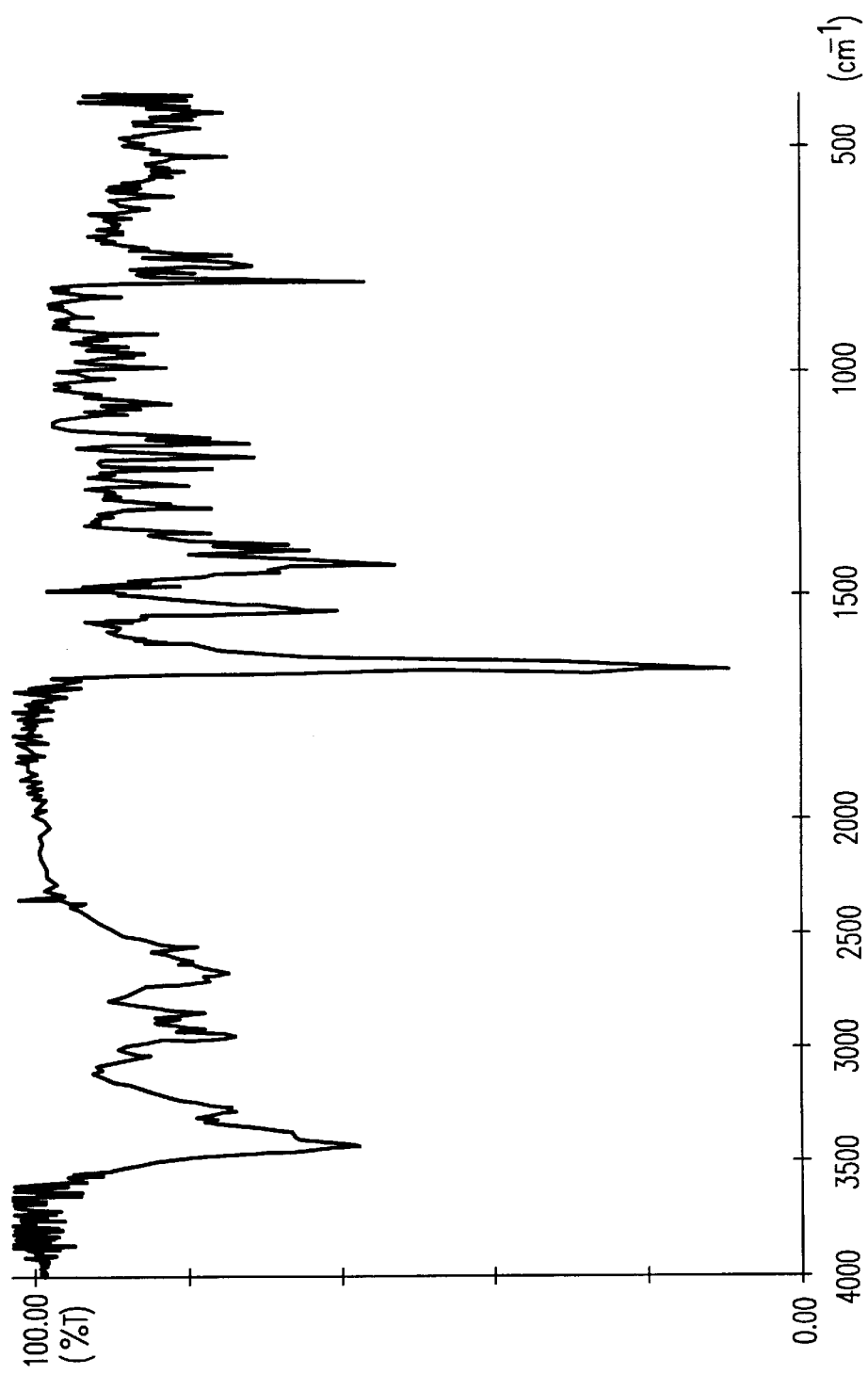
FIG. 7 is an IR absorption spectrum of α-type anhydride crystals.
Figure 8:
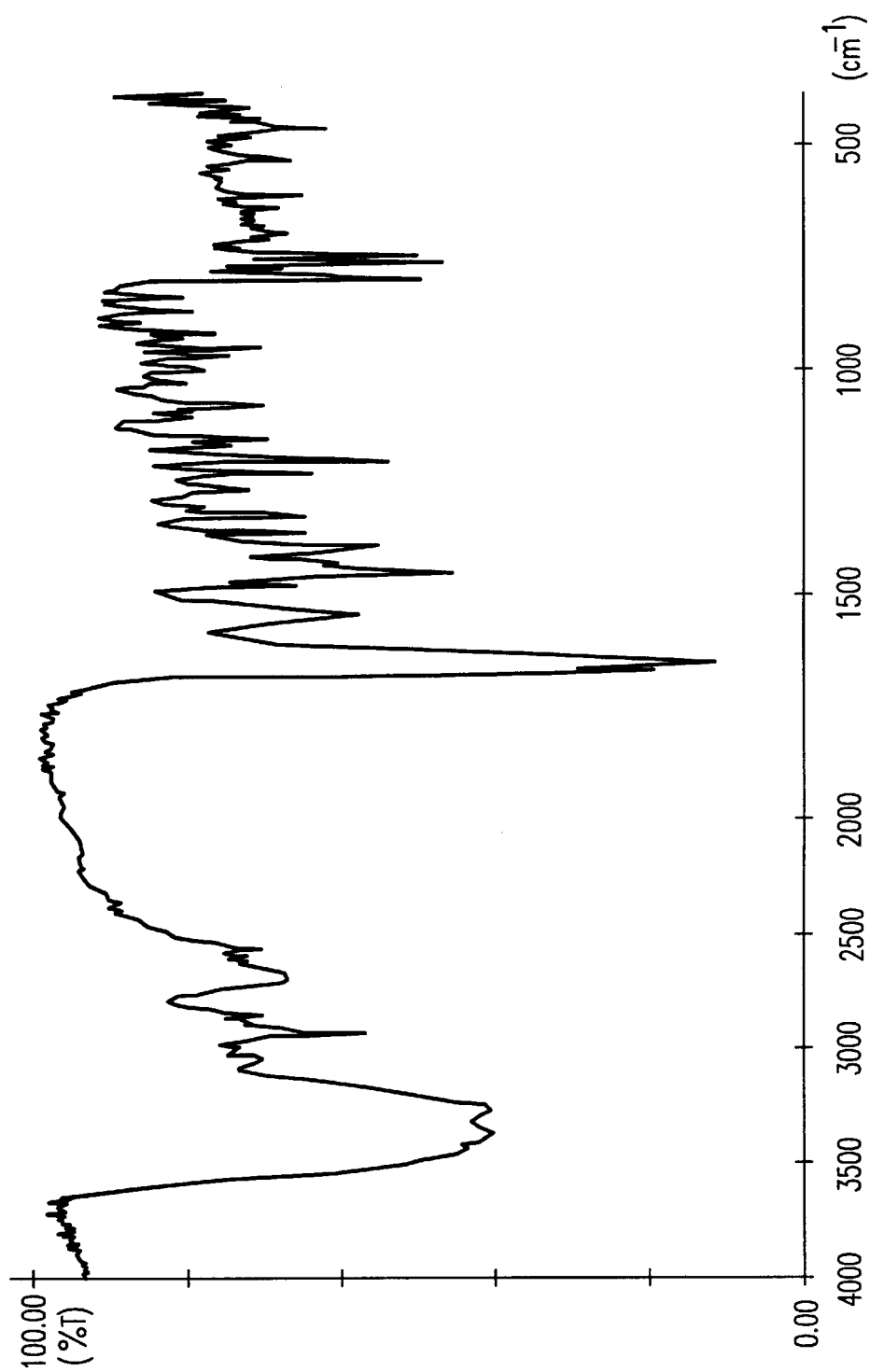
FIG. 8 is an IR absorption spectrum of β-type anhydride crystals.

The principal characteristics of these crystals are shown below. Powder X-ray diffraction patterns are shown in FIGS. 1 to 4. FIG. 1 is a powder X-ray diffraction pattern of monohydrate crystals. FIG. 2 is a powder X-ray diffraction pattern of trihydrate crystals. FIG. 3 is a powder X-ray diffraction pattern of anhydride crystals which are an intermediate for production of the monohydrate crystals (hereinafter referred to as α-type anhydride crystals). FIG. 4 is a powder X-ray diffraction pattern of anhydride crystals which are an intermediate for production of the trihydrate crystals (hereinafter referred to as β-type anhydride crystals). The diffraction angles (2θ) and intensities of the main peaks are shown in Tables 1 to 4.

TABLE 1

| 2θ | Intensity |
|---|---|
| 6.3 | medium |
| 10.5 | weak |
| 11.3 | medium |
| 11.8 | medium |
| 12.8 | weak |
| 13.3 | weak |
| 13.7 | weak |
| 14.3 | medium |
| 15.3 | weak |
| 16.1 | weak |
| 16.8 | medium |
| 17.7 | medium |
| 18.1 | weak |
| 18.7 | medium |
| 19.6 | medium |
| 20.3 | strong |
| 20.7 | medium |
| 21.2 | strong |
| 22.3 | weak |

TABLE 1-continued

| 2θ | Intensity |
|---|---|
| 22.8 | medium |
| 23.5 | weak |
| 24.4 | weak |
| 25.2 | medium |
| 25.6 | weak |
| 26.0 | medium |
| 26.4 | strong |
| 28.6 | weak |

TABLE 2

| 2θ | Intensity |
|---|---|
| 6.0 | medium |
| 10.2 | weak |
| 10.4 | weak |
| 10.9 | weak |
| 11.8 | weak |
| 12.2 | weak |
| 12.9 | medium |
| 13.4 | weak |
| 14.6 | strong |
| 16.3 | weak |
| 17.2 | weak |
| 18.2 | weak |
| 19.4 | weak |
| 19.6 | strong |
| 19.8 | medium |
| 20.7 | medium |
| 21.4 | weak |
| 21.8 | medium |
| 22.3 | medium |
| 22.9 | strong |
| 23.4 | weak |
| 24.1 | medium |
| 24.6 | weak |
| 26.0 | weak |
| 26.6 | medium |
| 27.3 | weak |
| 27.8 | medium |
| 28.3 | medium |
| 29.1 | medium |
| 29.7 | weak |
| 30.6 | weak |
| 32.3 | medium |

TABLE 3

| 2θ | Intensity |
|---|---|
| 6.3 | medium |
| 7.8 | weak |
| 9.4 | weak |
| 10.6 | weak |
| 11.3 | medium |
| 11.8 | medium |
| 12.9 | weak |
| 13.3 | weak |
| 13.8 | weak |
| 14.4 | weak |
| 15.3 | weak |
| 16.0 | weak |
| 16.9 | medium |
| 17.8 | medium |
| 18.1 | weak |
| 18.6 | medium |
| 19.4 | strong |
| 20.3 | strong |
| 20.9 | strong |

TABLE 3-continued

| 2θ | Intensity |
|---|---|
| 22.3 | weak |
| 22.7 | strong |
| 23.6 | weak |
| 25.1 | weak |
| 25.4 | weak |
| 26.0 | medium |
| 26.3 | strong |

TABLE 4

| 2θ | Intensity |
|---|---|
| 6.2 | medium |
| 7.8 | weak |
| 10.0 | weak |
| 10.8 | weak |
| 11.6 | weak |
| 12.0 | weak |
| 12.8 | medium |
| 13.7 | weak |
| 14.5 | weak |
| 15.0 | medium |
| 15.6 | medium |
| 16.6 | weak |
| 17.3 | weak |
| 18.0 | medium |
| 18.3 | weak |
| 18.9 | weak |
| 19.4 | medium |
| 20.6 | medium |
| 21.0 | weak |
| 21.6 | medium |
| 22.4 | strong |
| 23.8 | medium |
| 25.2 | weak |
| 25.6 | weak |
| 27.2 | medium |
| 27.9 | strong |
| 28.8 | weak |
| 29.4 | medium |
| 33.7 | medium |

IR absorption spectra are shown in FIGS. 5 to 8. No clear melting point was found for any of the above-mentioned four types of crystals.

The monohydrate crystals of Compound (I) in the present invention can be produced as follows.

Generally, the method of producing Compound (I) is not particularly limited. For example, this compound can be produced as schematically shown below using known reactants, reagents and reactions.

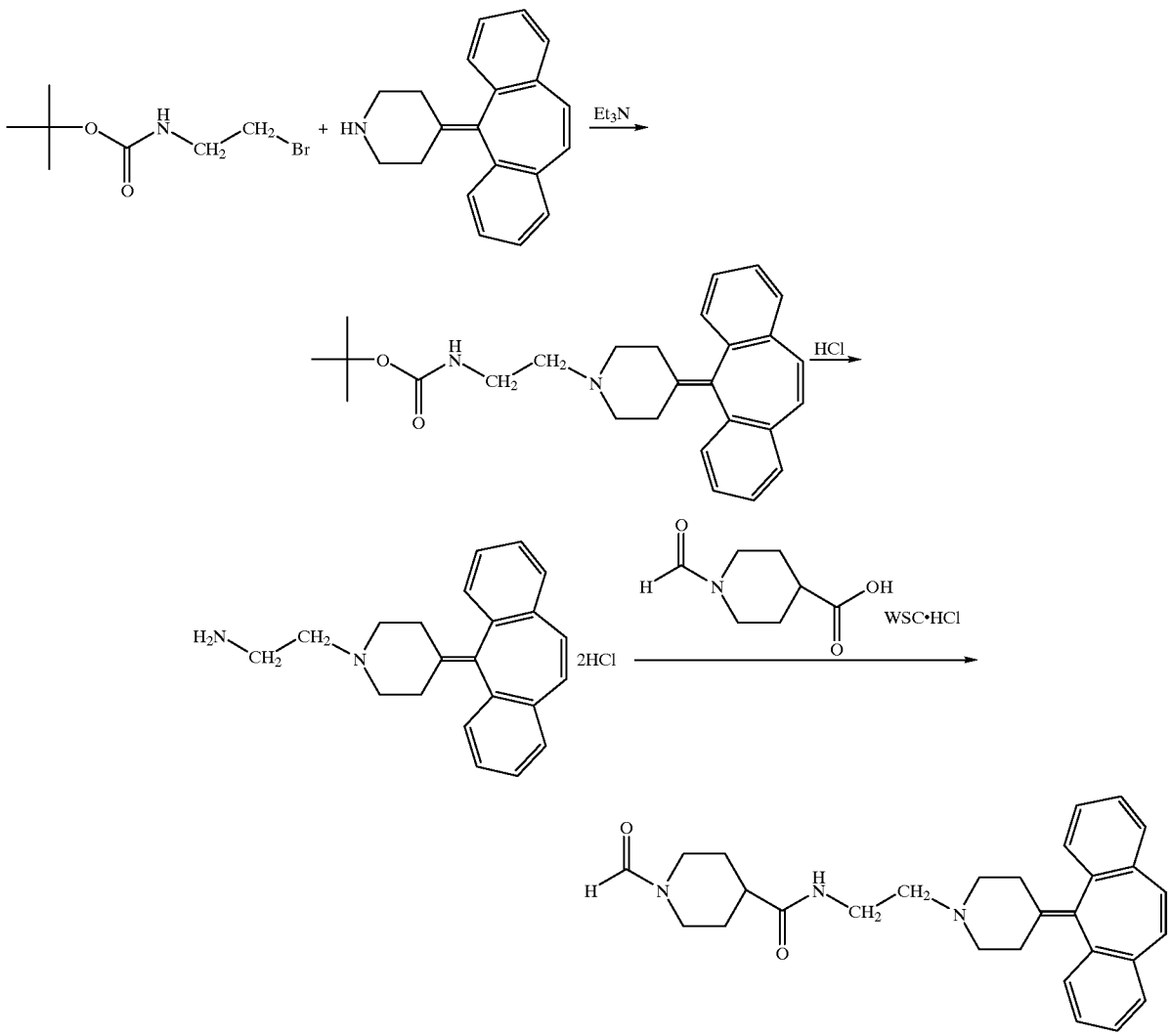

Compound (I) is dissolved in a mixed solvent of water with alcohol such as methanol, ethanol or isopropanol, tetrahydrofuran or acetone, and then crystallizing this compound through cooling or the like. At this point, the water content of the mixed solvent is preferably between about 2 and 50% by weight. The thus-obtained wet crystals are dried to obtain α-type anhydride crystals. Then when α-type anhydride crystals are kept under an appropriate temperature and appropriate humidity, dry monohydrate crystals can be obtained. At the humidity-controlling, the temperature is between 20 and 100° C., preferably between about 25 and 90° C., and the relative humidity is between about 10 and 100%, preferably between about 50 and 90%. The time utilized is between about 30 minutes and 48 hours, more preferably between about 2 hour and 30 hours. The phrase "humidity-control" means that crystals are kept or maintained under a certain temperature and humidity as defined herein.

The α-type anhydride crystals can be obtained by heat-drying the above-mentioned monohydrate crystals, or by dissolving the same crystals in the above-mentioned mixed solvent having a water content of less than 2% by weight, crystallizing the mixture, and drying the resulting crystals, or by dispersing the amorphous substance in a solvent such as ethyl acetate or acetone, treating the dispersion at from 10 to 50° C. for from 10 minutes to 48 hours, and after conversion to crystals, drying the crystals.

Further, the trihydrate crystals of Compound (I) of the present invention are hardly precipitated directly from the solvent. However, the trihydrate crystals can be obtained by precipitating the crystals from an aqueous solution, and humidity-controlling the resulting β-type anhydride crystals at an appropriate temperature and appropriate humidity. For the humidity-controlling, the temperature is between about 20 and 100° C., preferably between about 25 and 90° C., and the relative humidity is between about 30 and 100%, preferably between 50 and 90%.

The time utilized is between about 30 minutes and 48 hours, more preferably between about 2 hours and 30 hours.

The present invention will now be further illustrated by reference to the following Examples. These Examples are provided solely for purposes of illustration and are not intended to be limitative.

EXAMPLES

Production Example 1

Production of N-(2-(4-(5H-dibenzo[a,d]cyclohepten-5-ylidene)-piperidino)ethyl)-1-formyl-4-piperidinecarboxamide hydrochloride Step 1

2-Aminoethylbromide hydrobromide (35.77 g, 174.6 mmols) and 22.80 g (104.8 mmols) of di-tert-butyl dicarbonate were added to a mixed solvent of 300 ml of ether and 300 ml of water. Subsequently, 44.00 g (523.8 mmols) of sodium hydrogencarbonate were gradually added thereto, and the solution was stirred overnight at room temperature. The ether layer was washed with 80 ml of 1N hydrochloric acid and then with 80 ml of a saturated aqueous solution of sodium chloride, and dried over magnesium sulfate to obtain 21.57 g of 2-tert-butoxycarbonylaminoethyl bromide.

Step 2

2-Tert-butoxycarbonylaminoethyl bromide (13.5 g, 60.0 mmols) was dissolved in 900 ml of acetonitrile together with 8.1 g (30.0 mmols) of 4-(5H-dibenzo[a,d]cyclohepten-5-ylidene)piperidine and 12.6 ml (90 mmols) of triethylamine, and the mixture was reacted at 50° C. for 16 hours. After the temperature was returned to room temperature and the solvent was distilled off, the residue was dissolved in 900 ml of ethyl acetate, and insoluble matters were filtered off. The ethyl acetate solution was washed with 300 ml of 1N hydrochloric acid, with 300 ml of 1N sodium hydroxide and with 300 ml of a saturated aqueous solution of sodium chloride. After the resulting product was dried over magnesium sulfate, the solvent was distilled off, and the residue was purified through silica-gel chromatography to obtain 10.8 g of 4-(5H-dibenzo[a,d] cyclohepten-5-ylidene)-1-(2-tert-butoxycarbonylamino)ethyl) piperidine.

Step 3

4-(5H-dibenzo[a,d]cyclohepten-5-ylidene)-1-(2-tert-butoxycarbonylamino)ethyl)piperidine (8.47 g, 20.4 mmols) was dissolved in 100 ml of dichloromethane. Then, 100 ml of 4N hydrochloric acid dioxane solution were added thereto, and the resulting solution was stirred at room temperature for 1 hour. The solvent was distilled off to obtain 8.56 g of 1-(2-aminoethyl)-4-(5H-dibenzo[a,d] cyclohepten-5-ylidene)piperidine dihydrochloride.

Step 4

1-(2-Aminoethyl)-4-(5H-dibenzo[a,d]cyclohepten-5-ylidene)piperidine dihydrochloride (7.89 g, 20.3 mmols) was dissolved in 200 ml of dichloromethane. 1-Formylisonipecotic acid (3.68 g, 23.4 mmols), 15.3 ml (110.0 mmols) of triethylamine, 0.27 g (2.2 mmols) of 4-dimethylaminopyridine and 5.5 g (28.6 mmols) of 1-ethyl-3-(3-dimethylaminopropyl)-carbodiimide hydrochloride were added thereto, and the mixture was stirred overnight at room temperature. After the solvent was distilled off, the residue was dissolved in 100 ml of dichloromethane, and the solution was washed with 100 ml of 1N hydrochloric acid, with 100 ml of 1N sodium hydroxide and with 50 ml of a saturated aqueous solution of sodium chloride. The solvent was distilled off, and the residue was purified through silica-gel chromatography to obtain 5.9 g of N-(2-(4-(5H-dibenzo[a,d]cyclohepten-5-ylidene)-piperidine)ethyl)-1-formyl-4-piperidinecarboxamide.

Step 5

N-(2-(4-(5H-dibenzo[a,d]cyclohepten-5-ylidene)-piperidine)ethyl)-1-formyl-4-piperidinecarboxamide (5.90 g, 13.0 mmols) was dissolved in 50 ml of ether. Four milliliters of 4N hydrochloric acid dioxane were added thereto dropwise in an ice-water bath while being stirred. one hundred milliliters of ether were added thereto, and the mixture was stirred for 1 minute. Then, insoluble matters were separated through filtration. The filtrate was dried under reduced pressure at 80° C. for 8 hours to give 5.14 g of N-(2-(4-(5H-dibenzo[a,b]cyclohepten-5-ylidene)-piperidine)ethyl)-1-form yl-4-piperidinecarboxamide hydrochloride. This compound was amorphous.

Example 1

Compound (I) (1.2 g) was dissolved in 3 ml of ethanol at 60° C., and the solution was gradually cooled to 20° C. while being stirred. The crystals precipitated were collected through filtration, and were dried at 60° C. under reduced pressure to obtain 0.4 g of the dry crystals. Elemental analysis and powder X-ray diffraction pattern of the crystals indicated that these crystals were α-type anhydride crystals.

Example 2

Compound (I) (0.5 g) was dispersed in 10 ml of ethyl acetate, and the dispersion was stirred at 40° C. for 48 hours. The crystals were collected through filtration, and were dried at 60° C. under reduced pressure to obtain 0.48 g of the dry crystals. Elemental analysis and powder X-ray diffraction pattern of the crystals indicated that these crystals were α-type anhydride crystals.

Example 3

The α-type anhydride crystals obtained in Example 1 were spread thin on a petri dish, and were allowed to stand in a vessel which had been controlled at 40° C. and relative humidity of 75%. After 24 hours, the crystals were subjected to elemental analysis and powder X-ray diffraction, from which it was determined that the crystals were monohydrate crystals.

Example 4

Compound (I) (77.5 g) was dissolved in 610 ml of ethanol at 20° C., and 22 ml of water were added thereto. The solution was cooled to 10° C. while being stirred, and the reaction solution was further stirred for 16 hours. The crystals formed were collected through filtration. At this time, the crystals were monohydrate crystals. These crystals were dried at 70° C. under reduced pressure to obtain 61.54 g of α-type anhydride crystals. The resulting crystals were allowed to stand overnight at room temperature in a desiccator which had been controlled at relative humidity of 75% with a saturated aqueous solution of sodium chloride to give 63.8 g of the crystals. Elemental analysis and powder X-ray diffraction pattern of the crystals indicated that these crystals were monohydrate crystals.

Example 5

One gram of Compound (I) was dissolved in 10 ml of water at 80° C., and the solution was gradually cooled while being stirred. The cooling was conducted until the temperature reached 20° C. The crystals precipitated were collected through filtration, and were dried overnight at 60° C. under reduced pressure to obtain 0.85 g of the dry crystals. Elemental analysis and powder X-ray diffraction pattern of the crystals indicated that these crystals were β-type anhydride crystals.

Example 6

The β-type anhydride crystals obtained in Example 5 were spread thin on a petri dish, and were allowed to stand in a temperature and humidity chamber which had been controlled at 40° C. and relative humidity of 75%. After 24 hours, the crystals were subjected to elemental analysis and powder X-ray diffraction, from which it was determined that the crystals were trihydrate crystals.

Example 7

A suspension of compound (I) (53.6 g) in isopropyl alcohol was stirred at 53° C. in 30 min, and then gradually cooled to 20° C. while being stirred. The crystals precipitated were collected through filtration, and were dried under reduced pressure to obtain 051.4 g of the anhydrous crystals. The resulting crystals were allowed to stand overnight at room temperature in a desiccator which had been humidity-controlled at relative humidity of 75% to gave 52.5 g of the crystals. Elemental analysis and powder X-ray diffraction pattern of the crystals indicated that these crystals were monohydrate crystal.

Example 8

The α-type anhydride crystals (2718 g) prepared by a similar method of Example 1 were powdered by mill, and were allowed to stand in a seal-up box which had been controlled at 30° C. and relative humidity of 80%. After 23 hours, the crystals were subjected to elemental analysis and powder X-ray diffraction, from which it was determined that the crystals were monohydrate crystals (2776 g).

Test Example 1

Each of the monohydrate and trihydrate crystals of Compound (I) produced in Examples 4 and 6 was orally administered to a Beagle dog at a dose of 3.0 mg/kg. After 30 minutes, 1 hour, 2 hours, 3 hours, 4 hours, 6 hours, 8 hours and 24 hours of the administration, the blood was collected, the concentration of Compound (I) in the plasma was measured, and the area under plasma concentration curve (AUC) was obtained. When the ratio of the AUC value of oral administration to that of intravenous administration was defined as bioavailability, the bioavailability of the monohydrate crystals was 73.4%, and that of the trihydrate crystals was 49.6%. Thus, the bioavailability of the monohydrate crystals was higher than that of the trihydrate crystals, and the monohydrate crystals, thus, exhibited high oral absorption.

Test Example 2

Figure 9:
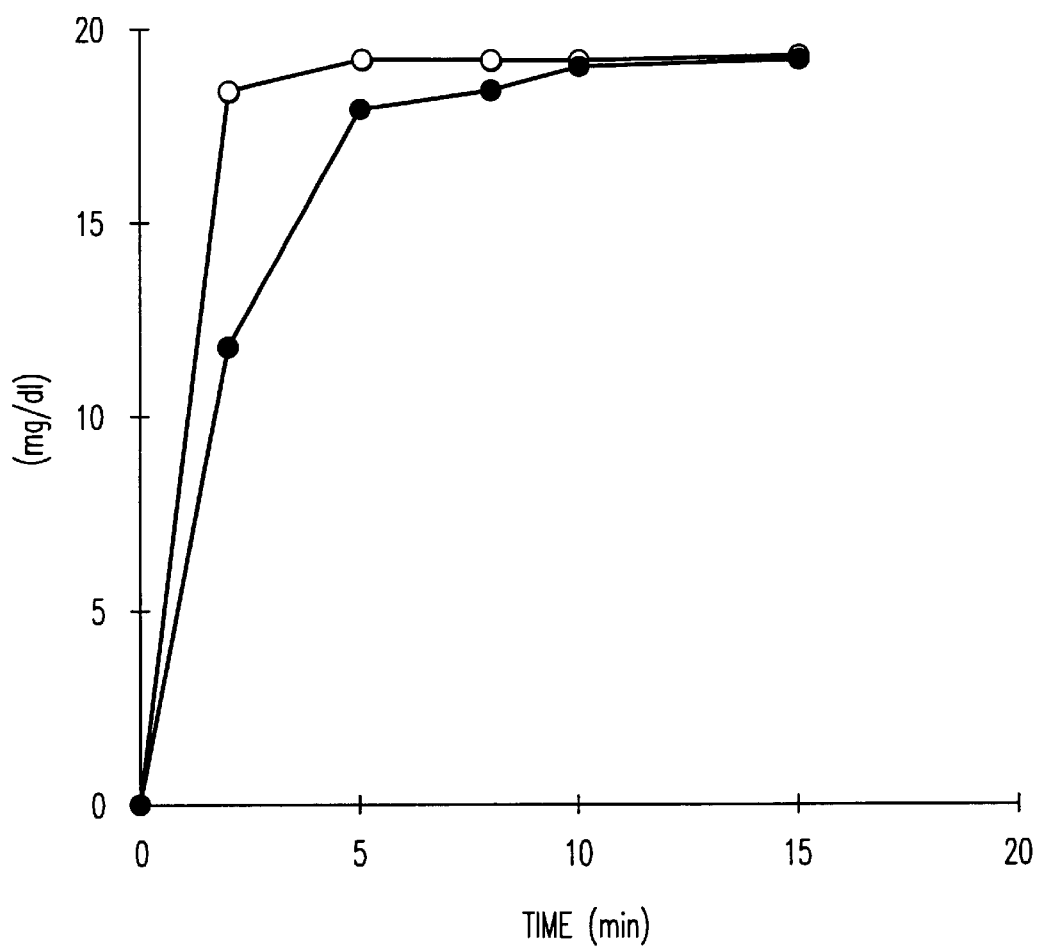
FIG. 9 is a graph showing curves of dissolution rates of monohydrate and trihydrate crystals. The indication "●" corresponds to a datum point on a curve of a dissolution rate of monohydrate crystals, and the indication "○" corresponds to a datum point on a curve of a dissolution rate of trihydrate crystals.

Each 20 mg of the monohydrate and trihydrate crystals of Compound (I) produced in Examples 4 and 6 was added to 500 ml of a gastric juice model solution (JP-1 solution according to Japan Pharmacopeia) of 37° C., and the concentration of Compound (I) in the solution was measured over the course of time. The results are shown in FIG. 9. From FIG. 9, it was estimated that the trihydrate crystals exhibited a high dissolution rate compared to the monohydrate crystals and are, thus, suited for the production of prompt release drug products.

The monohydrate and trihydrate crystals of the present invention exhibit surprisingly high stability, as they remain chemically and physically, unchanged even after storage for 1 month. Further, the monohydrate crystals exhibit excellent oral absorption, while the trihydrate crystals exhibit a high dissolution rate, making it possible to form preparations that meet various requirements. Still further, the monohydrate and trihydrate crystals of the present invention can be easily produced from α-type anhydride crystals and β-type anhydride crystals.

It will be understood that many changes and modifications may be made to the above-described embodiments without departing from the spirit and scope of the present invention.

What is claimed as new and desired to be secured by Letters Patent of the United States is:

1. Crystals of N-(2-(4-(5H-dibenzo(a,d)cyclohepten-5-ylidene)-piperidino)ethyl)-1-formyl-4-piperidinecarboxamide hydrochloride trihydrate.

2. The crystals of claim 1, wherein peaks are present at diffraction angles (2θ±0.1) of 14.6, 19.6, 21.8, 22.3, 22.9, 24.1, 26.6 and 28.3° in powder X-ray diffraction.

3. Crystals of N-(2-(4-(5H-dibenzo[a,d]cyclohepten-5-ylidene)-piperidino)ethyl)-1-formyl-4-piperidinecarboxamide hydrochloride anhydride, wherein peaks are present at diffraction angles (2θ±0.1) of 12.8, 15.0, 19.4, 22.4, 23.8, 27.2 and 27.9° in powder X-ray diffraction.

4. A process for producing the crystals of N-(2-(4(5H-dibenzo[a,d]cyclohepten-5-ylidene)-piperidino)ethyl)1-formyl-4-piperidinecarboxamide hydrochloride trihydrate, which comprises crystallization of the anhydride of claim 3 in a temperature and humidity controlled chamber.

5. The process of claim 4, wherein the temperature is maintained at from 20 to 90° C.

6. The process of claim 5, wherein the temperature is maintained at from about 25° C. and 90° C.

7. The process of claim 4, wherein the relative humidity is maintained at from 50 to 100%.

8. The process of claim 7, wherein the relative humidity is maintained at from about 50 to 90%.

* * * * *